(12) United States Patent
Koarashi

(10) Patent No.: US 12,076,508 B2
(45) Date of Patent: Sep. 3, 2024

(54) FIXING DEVICE

(71) Applicant: HI-LEX Corporation, Takarazuka (JP)

(72) Inventor: Shinsaku Koarashi, Hyogo (JP)

(73) Assignee: HI-LEX CORPORATION, Takarazuka (JP)

( * ) Notice: Subject to any disclaimer, the term of this patent is extended or adjusted under 35 U.S.C. 154(b) by 742 days.

(21) Appl. No.: 17/285,274

(22) PCT Filed: Oct. 21, 2019

(86) PCT No.: PCT/JP2019/041247
§ 371 (c)(1),
(2) Date: Apr. 14, 2021

(87) PCT Pub. No.: WO2020/085274
PCT Pub. Date: Apr. 30, 2020

(65) Prior Publication Data
US 2021/0370024 A1    Dec. 2, 2021

(30) Foreign Application Priority Data

Oct. 22, 2018  (JP) .................................. 2018-198455

(51) Int. Cl.
*A61M 25/02* (2006.01)
*A61M 60/104* (2021.01)
*A61M 60/859* (2021.01)

(52) U.S. Cl.
CPC ....... *A61M 25/02* (2013.01); *A61M 2025/028* (2013.01); *A61M 2025/0286* (2013.01); *A61M 60/104* (2021.01); *A61M 60/859* (2021.01)

(58) Field of Classification Search
CPC .. A61M 25/02; A61M 60/104; A61M 60/859; A61M 60/861; A61M 2025/028;
(Continued)

(56) References Cited

U.S. PATENT DOCUMENTS 3,783,868 A * 1/1974 Bokros ............. A61M 39/0247
623/1.42
5,971,962 A  10/1999 Kojima et al.
(Continued)

FOREIGN PATENT DOCUMENTS

CN        101389293 A    3/2009
CN        104548284 A    4/2015
(Continued)

OTHER PUBLICATIONS

English translation of Written Opinion of the International Searching Authority accompanying the International Preliminary Report on Patentability, notification mailed May 6, 2021, International Application No. PCT/JP2019/041247 filed Oct. 21, 2019, 6 pages total.

(Continued)

*Primary Examiner* — Scott J Medway
*Assistant Examiner* — Anh Bui
(74) *Attorney, Agent, or Firm* — Ware, Fressola, Maguire Barber LLP

(57) ABSTRACT

A fixing device capable of being fixed, by simple fixing, to a living body without causing an occurrence of inflammation is provided. The fixing device 3 is fixed beneath the skin of the living body and includes a porous portion 31a capable of inducing cells thereto and a flat portion 31b that allows the cells to be adhered thereto, the porous portion 31a and the flat portion 31b are provided adjacent to each other, and a virtual surface SF1 of the porous portion 31a and a surface SF2 of the flat portion 31b are substantially flush with each other.

6 Claims, 4 Drawing Sheets

(58) Field of Classification Search
CPC .......... A61M 2025/0286; A61M 39/02; A61M 39/0247; A61M 2039/0261
See application file for complete search history.

(56) References Cited

U.S. PATENT DOCUMENTS

| | | |
|---|---|---|
| 2009/0192464 A1 | 7/2009 | Axelsson et al. |
| 2012/0302959 A1 | 11/2012 | Fielder et al. |
| 2014/0364880 A1 | 12/2014 | Farnan et al. |
| 2021/0402150 A1* | 12/2021 | Koarashi ............... A61M 60/88 |

FOREIGN PATENT DOCUMENTS

| | | | |
|---|---|---|---|
| JP | 2011188989 A | * | 9/2011 |
| JP | 2017-104437 A | | 6/2017 |

OTHER PUBLICATIONS

English translation of the International Search Report, PCT/JP2019/041247, Jan. 7, 2020, 1 page.

Notification of First Office Action dated May 30, 2022 for Chinese Patent Application No. 201980069045.5 received from CNIPA in Chinese language, with a list of five cited documents (D1-D5) with relevance categories indicated on pp. 6 and 7 (D1 & D2 already cited on prior IDS on Apr. 14, 2021), 7 pages total.

English language translation of pp. 1 and 2 and Examiner's Comments on pp. 3 and 4 of Chinese language "Notification of First Office Action" for Application No. 201980069045.5 dated May 30, 2022 from CNIPA (NPL Cite No. 1), 5 pages total.

* cited by examiner

FIXING DEVICE

TECHNICAL FIELD

The invention relates to a fixing device.

BACKGROUND ART

A tubular body (for example, a medical tube), which is to be inserted through the living body and communicates the inside and the outside of the living body, is held to the living body by a holding structure for holding the tubular body to an insertion target.

As such a holding structure, a holding structure in which a tubular body is held in a liquid-tight manner by a fixing member being fixed to the skin is disclosed, such as a holding structure assembly disclosed in Patent document 1, for example. The above-mentioned holding structure realizes a high adhesion between the fixing member and the tubular body by, screwing a male screw portion of a screw member into a female screw portion of the inserting portion when a fixing member-side contacting portion of a chuck member contacts the inserting portion inclination surface of an inserting portion.

PRIOR ART DOCUMENT

Patent Document

Patent Document 1: JP 2017-104437 A

SUMMARY OF THE INVENTION

Problem to be Solved by the Invention

Such a holding structure assembly has a fixing portion being a part to be fixed to the living body. The surface of the fixing portion is formed of a porous material allowing invasion of cells thereinto, such as titanium fiber having a good biocompatibility to achieve fixing of the fixing portion to the living body owing to adhesion between the fixing portion and the skin. However, while the cells easily invade into the porous material, substances inhibiting fixing of the fixing portion to the living body, such as bacteria, also easily invade thereinto, so that, in a case the substances inhibiting fixing thereof to the living body invade thereinto, they are likely to cause an occurrence of inflammation in biological tissues. Therefore, to fix the porous material to the living body, management using a special protection such as covering the porous material with a film so that the bacteria possibly causing the occurrence of inflammation is not brought into contact therewith is necessary. Such management is likely to cause troubles in daily life, so that it is desired to provide a fixing device such that the porous material can be fixed to the living body by simple fixing to the living body without requiring such a special protection.

An object of the invention is to provide a fixing device that can be fixed, by simple fixing, to the living body without causing an occurrence of inflammation.

Means to Solve the Problem

A fixing device according to the invention is a fixing device to be fixed beneath the skin of the living body. The fixing device comprising a porous portion capable of inducing cells to the porous portion and a flat portion that allows the cells to be adhered to the flat portion, the porous portion and the flat portion are provided adjacent to each other, and a virtual surface of the porous portion and a surface of the flat portion are substantially flush with each other.

Effects of the Invention

The fixing device according to the invention makes it possible to be fixed, by simple fixing, to the living body without causing an occurrence of inflammation.

EMBODIMENT FOR CARRYING OUT THE INVENTION

Below, a fixing device according to one embodiment of the invention is explained with reference to the attached drawings. The embodiment shown below is merely one example, so that a fixing device in the invention is not limited to the embodiment below.

First, a holding mechanism assembly including a fixing device according to one embodiment of the invention will be explained.

The holding mechanism assembly is a structure for holding an inserting member to be inserted through an insertion target. Here, "insert" means that the inserting member having a predetermined length is at least in a state in which the inserting member is present across the interior and the exterior of the holding mechanism assembly. As long as the inserting member is inserted through the insertion target, the inserting member may pass through the insertion target or not pass through the insertion target. The insertion target has a hole through which the inserting member is to be inserted. The inserting member has a predetermined length.

For the inserting member, a flexible medical tube may be used as one example. In the embodiment, a driveline being one type of medical tube is used. The above-mentioned driveline is inserted from tissues outside the living body, such as the skin into inside the body, such as an organ. The inserting member is not limited to the driveline, so that the inserting member may be a catheter, a different medical tube, or a solid medical cable, or may be a different member having a predetermined length.

<Configuration of Holding Mechanism Assembly>

Next, the overall configuration of the holding mechanism assembly will be explained using FIGS. 1 and 2.

Figure 1:
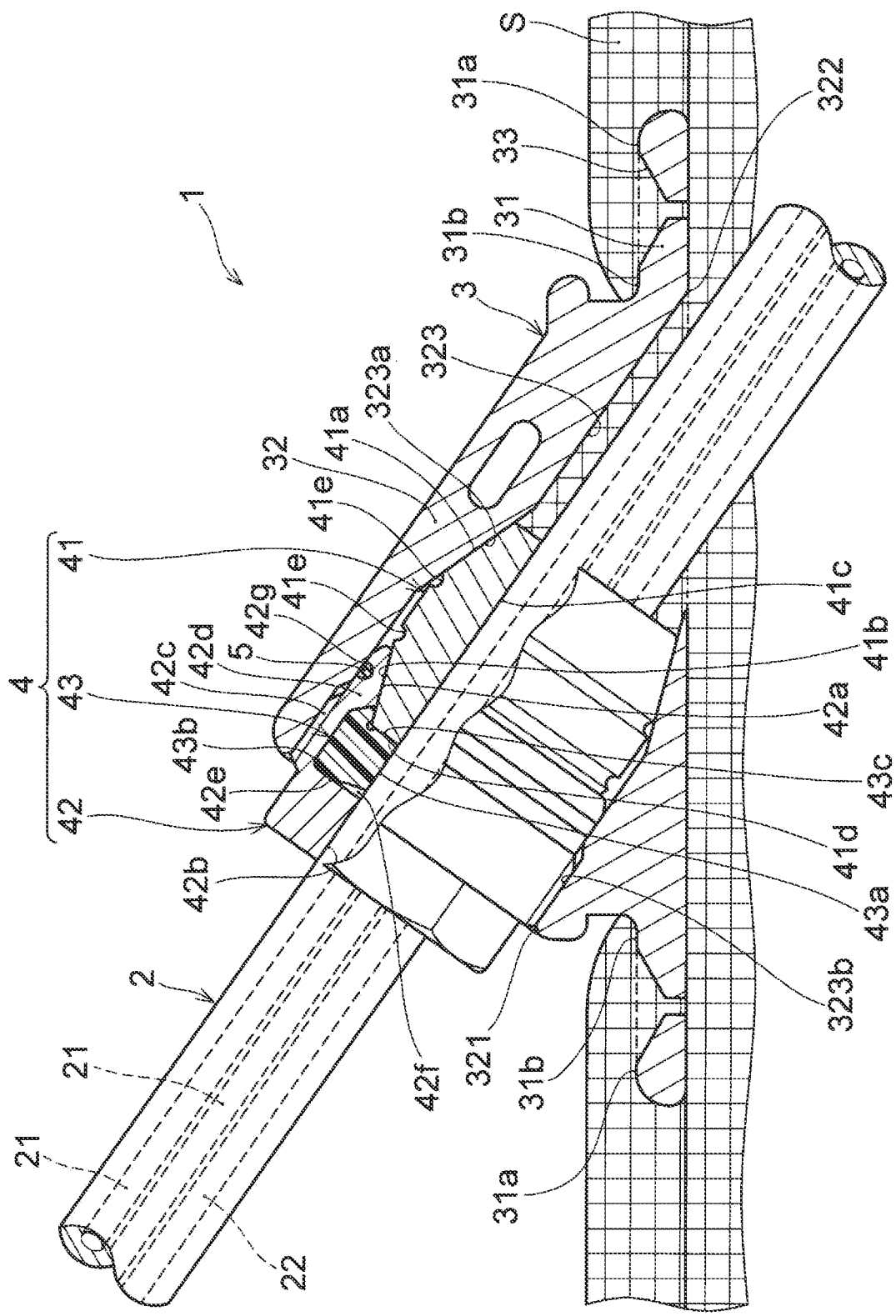
FIG. 1 shows a lateral partial cross-sectional view of an overall configuration of a holding mechanism assembly including a fixing device according to one embodiment of the invention.

As shown in FIG. 1, a holding mechanism assembly 1 comprises a driveline 2 being an inserting member; a fixing device 3 to fix the driveline 2 with respect to a skin S; and a holding structure 4 to hold the driveline 2 to the fixing device 3 in a liquid-tight manner. Here, the fixing device 3 is fixed to the skin S by anchoring (fixing) a part of the skin S to the surface of the fixing device 3.

The driveline 2 is a tubular member. The outer surface of the driveline 2 is covered with fiber. An end of the driveline 2 inside the body is coupled to a medical device (not shown) being arranged in the body. An end of the driveline 2 outside the body is coupled to a device (not shown) being arranged outside the body. A connector (not shown) for coupling a device (not shown) may be mounted to the end of the driveline 2 outside the body. The outer diameter of the connector may be greater or less than the outer diameter of the driveline 2.

In the embodiment, the medical device arranged inside the body is an auxiliary artificial heart. The auxiliary artificial heart is a member having a pump to circulate blood in the body. The device arranged outside the body includes a pressure-feeding pump to send out cooling water to cool the above-mentioned pump and a power source to feed electric power to the pump. The driveline 2 has, in the interior thereof, a cooling water circulation path 21 to circulate cooling water between the pressure-feeding pump and the auxiliary artificial heart, and a power cable 22 to connect the power source and the pump. The configuration of the driveline 2 is not limited thereto, so that a publicly-known configuration may be adopted. For example, the driveline 2 may be configured to have only a power cable, may be configured to have only a cooling water circulation path, or may be configured to have a member having a different function. The driveline 2 includes the cooling water circulation path 21 containing water inside thereof and the power cable 22, and is used as a medical tube having flexibility and rigidity.

The fixing device 3 has a fixing portion 31 to be fixed to the skin S and a communicating portion 32 through which the driveline 2 is inserted. The fixing portion 31 of the fixing device 3 will be described below.

The communicating portion 32 communicates the inside of the living body and the outside of the living body. In the embodiment, the communicating portion 32 is a portion through which an inserting member such as the driveline 2 is inserted and is configured in a substantially cylindrical shape. The communicating portion 32 has an opening for the inside of the living body and an opening for the outside of the living body. The communicating portion 32 has a first opening 321, a second opening 322, a communication path 323 to communicate the first opening 321 and the second opening 322, a communicating portion inclined surface 323a provided at the inner surface of the communication path 323 such that the inner diameter is reduced from the first opening 321 toward the second opening 322, and a female screw portion 323b provided on the inner peripheral surface of the first opening 321. In each of the drawings, illustration of the screw groove of the female screw portion 323b is omitted.

The first opening 321 is an opening to be provided at the outside of the living body of the communicating portion 32, while the second opening 322 is an opening to be provided at the inside of the living body. The first opening 321 is formed such that the opening surface thereof is orthogonal with respect to the axial direction of the communicating portion 32. The second opening 322 is formed such that the opening surface thereof is non-orthogonal with respect to the axial direction of the communicating portion 32. The cross section of the first opening 321 is formed in a circular shape, and the diameter of the first opening 321 in the cross section is substantially the same as the outer diameter of a screw member 42 to be described below. The cross section of the second opening 322 is formed in an elliptical shape, and the cross-sectional area of the second opening 322 is formed to be greater than the cross-sectional area of the driveline 2 when the driveline 2 is cut in a direction being parallel to the second opening 322.

The communication path 323 is a path to communicate the first opening 321 and the second opening 322. The communication path 323 is formed in a circular shape in a cross sectional view. The communication path 323 is configured such that the central axis thereof forms one straight line. While the communication path 323 is formed such that the central axis thereof forms one straight line, it is not limited thereto. The communication path 323 may be formed to be curved or bent at the intermediate portion of the communication path 323, for example. Moreover, in the embodiment, the communication path 323 is configured to be inclined with respect to the fixing portion 31, but the inclined angle is not particularly limited. Furthermore, the communication path may be formed to be orthogonal to the target.

The communicating portion inclined surface 323a is a portion provided on the inner surface of the communication path 323 and is provided such that the inner diameter thereof is reduced toward the second opening 322 from the first opening 321. The communicating portion inclined surface 323a is provided such that the inclined angle of the communicating portion inclined surface 323a is constant. In other words, the communicating portion inclined surface 323a is configured in a straight-line shape in the cross section shown in FIG. 1. While the communicating portion inclined surface 323a is formed such that the inclined angle thereof is constant in the embodiment, it is not limited thereto. For example, the communicating portion inclined surface 323a may also be formed such that the inclined angle of the communicating portion inclined surface 323a increases toward the second opening 322. In this case, the communicating portion inclined surface is configured such that the cross section shown in FIG. 1 is in a curved shape.

The female screw portion 323b is a portion provided on the inner peripheral surface of the first opening 321. A male screw portion 42c to be described below screws into the female screw portion 323b.

In the embodiment, the holding structure 4 is a structure so that the fixing device 3 holds the driveline 2 in a liquid-tight manner to keep inside of the body in a liquid-tight manner. The holding structure 4 comprises a chuck member 41, a screw member 42, and a sealing member 43.

The chuck member 41 is a member to tighten and grasp an inserting member such as the driveline 2. The chuck member 41 has a fixing device-side contacting portion 41a which is provided on an outer periphery of one end side of the chuck member 41 and contacts the communicating portion inclined surface 323a, a screw member-side contacting portion 41b which is provided on an outer peripheral surface on the other end side of the chuck member 41 and contacts the screw member 42, a fitting portion 41c which is provided on the inner side and fits to the outer periphery of the driveline 2 in close contact therewith, and a sealing member-side contacting portion 41d to contact the sealing member 43. The chuck member 41 is a member to be arranged between the inner peripheral surface of the communicating portion 32 and the outer peripheral surface of the driveline 2. The chuck member 41 has, in the holding structure 4, a role of holding the driveline 2 by tightening the driveline 2 and a role of achieving liquid tightness. A material for the chuck member is not particularly limited. A material capable of being slightly deformed such as to make it possible to tighten the driveline 2 may be used as a material capable of achieving the role of holding the insertion target and the role of achieving the liquid tightness. The chuck member 41 in the embodiment is formed of a metal having a high corrosion resistance, which metal has the hardness equivalent to that of a material forming the fixing device 3 or the hardness lower than that of the material forming the fixing device 3. The metal having the high corrosion resistance may be titanium or a titanium alloy, for example.

In a state where the chuck member 41 is arranged in the communicating portion 32, the fixing device-side contacting portion 41a is a contacting portion provided at an end on the second opening 322 side and is a portion which contacts the communicating portion inclined surface 323a. The fixing device-side contacting portion 41a is configured to contact the communicating portion inclined surface 323a such that a force in a direction in which the chuck member 41 is reduced in diameter (a force toward the driveline 2) is applied to the chuck member 41 from the communicating portion inclined surface 323a. In the embodiment, the inclined angle of the fixing device-side contacting portion 41a is identical to that of the communicating portion inclined surface 323a. In other words, the fixing device-side contacting portion 41a is configured to contact the communicating portion inclined surface 323a in a surface contact with the communicating portion inclined surface 323a. In other words, an inclined surface having identical inclined angle to that of the communicating portion inclined surface 323a is preferably formed in at least one portion of the fixing device side contacting portion 41a.

The screw member-side contacting portion 41b is a contacting portion provided at an end on the first opening 321 side in a state where the chuck member 41 is arranged in the communicating portion 32 to contact the screw member 42. The screw member-side contacting portion 41b is configured as a part of an inclined surface formed on the first opening 321 side of the chuck member 41. The screw member-side contacting portion 41b is configured to contact the tip contacting portion 42a of the screw member 42 (described below) such that a force in the direction in which the chuck member 41 is reduced in diameter (a force toward the driveline 2) is applied to the chuck member 41 from the tip contacting portion 42a. Moreover, the tip contacting portion 42a of the screw member 42 also receives, from the screw member-side contacting portion 41b, a force outwardly in a radial direction of the screw member 42. In the embodiment, the screw member-side contacting portion 41b is configured by an inclined surface whose inclined angle is identical to that of the tip contacting portion 42a being an inclined surface. In other words, the screw member-side contacting portion 41b is configured to contact the tip contacting portion 42a in a surface contact with the tip contacting portion 42a. In other words, an inclined surface having inclined angle identical to that of the tip contacting portion 42a is preferably formed in at least one portion of the screw member-side contacting portion 41b.

While the screw member-side contacting portion 41b is configured with an inclined surface, it is not limited thereto. It suffices that the screw member-side contacting portion 41b has a shape capable of receiving a force from the screw member 42 in a direction in which the chuck member 41 is at least pushed toward the second opening 322 side.

The fitting portion 41c is a portion to fit to the outer periphery of the driveline 2 in close contact therewith. In the embodiment, the fitting portion 41c is the entire inner peripheral surface of the chuck member 41. In the embodiment, the chuck member 41 has a communicating hole to communicate an opening at a side of the first opening 321 and an opening at a side of the second opening 322 and grasps the driveline 2 such that the driveline 2 extends out of these openings, and the fitting portion 41c is the entire inner peripheral surface of the communicating hole of the chuck member 41.

The fitting portion 41c is formed in a circular shape in a cross section and is formed such that the diameter of the cross section of the fitting portion 41c is uniform as shown in FIG. 1. While the fitting portion 41c is formed such that the diameter of the cross section thereof is uniform, it is not limited thereto. The fitting portion 41c may have a step portion formed such that the diameter of the cross section increases in the central region of the fitting portion 41c, for example.

The sealing member-side contacting portion 41d is a contacting portion provided at an end on the first opening 321 side in a state where the chuck member 41 is arranged in the communicating portion 32 to contact the sealing member 43. The sealing member-side contacting portion 41d is configured with a part of the inclined surface formed on the first opening 321 side of the chuck member 41 and a surface being parallel to the radial direction of the communicating portion 32. The sealing member-side contacting portion 41d is continuously formed with the screw member-side contacting portion 41b. While the sealing member-side contacting portion 41d is configured with the part of the inclined surface formed on the first opening 321 side of the chuck member 41 and the surface being parallel to the radial direction of the communicating portion 32, it is not limited thereto. It suffices that the sealing member-side contacting portion 41d has a shape capable of receiving a force from the sealing member 43 in a direction in which the chuck member 41 is pushed toward the second opening 322 side.

Figure 2:
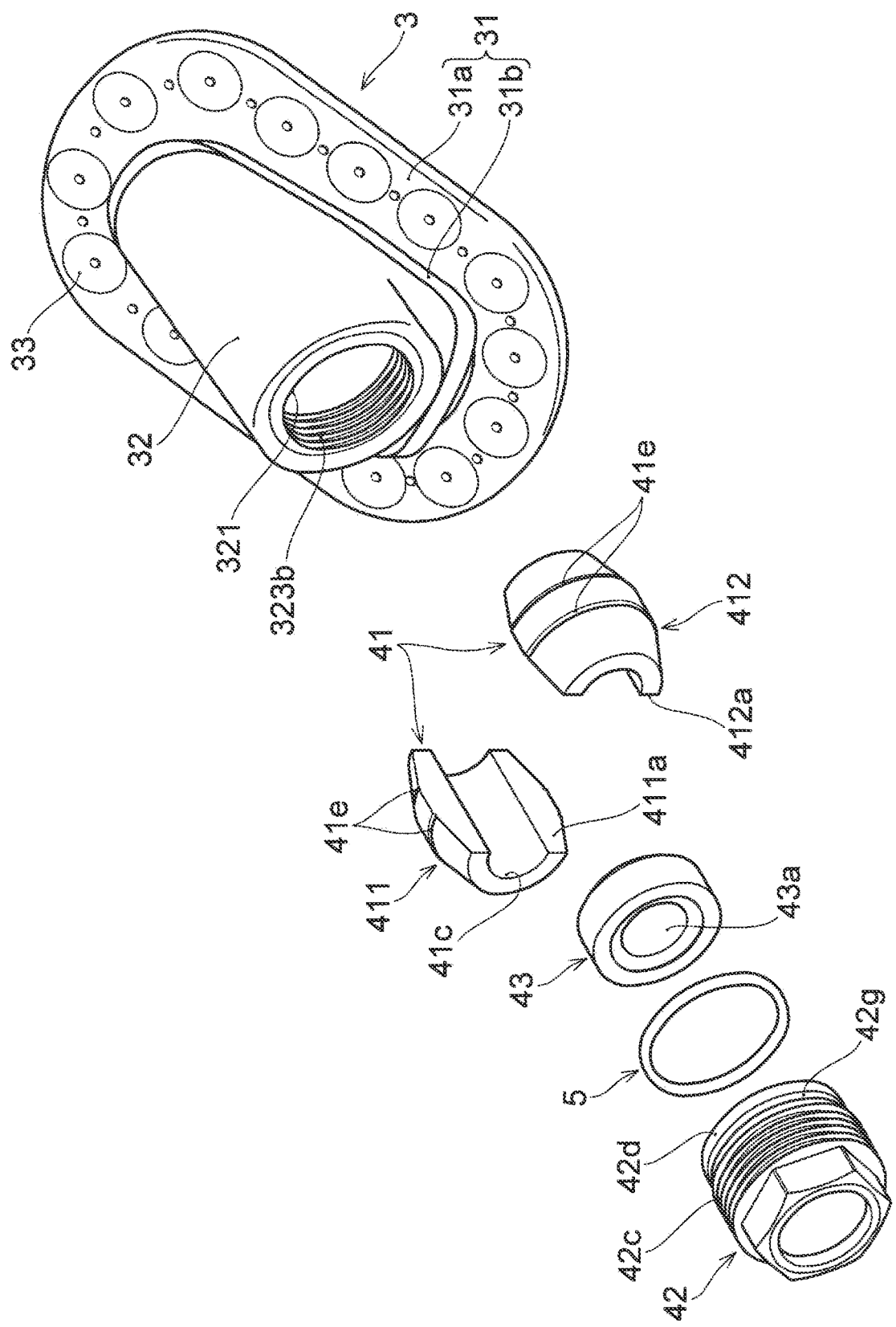
FIG. 2 shows an exploded perspective view of the holding mechanism assembly in FIG. 1.

As shown in FIG. 2, the chuck member 41 in the embodiment configured by a first chuck member 411 and a second chuck member 412. The chuck member 41 may be divided in the radial direction and may be a substantially tubular body by integrally joining them. The chuck member 41 is formed when a joining surface 411a of the first chuck member 411 and a joining surface 412a of the second chuck member 412 are joined. Moreover, the chuck member 41 has a concave portion 41e on the outer peripheral surface of the chuck member 41. The concave portion 41e is provided in order to stop sliding of the chuck member 41 when the chuck member 41 is attached to the insertion target. The structure of the chuck member 41 is not limited to the structure capable of being divided in the radial direction. The chuck member 41 may be configured as the structure capable of being divided in the axial direction or the structure not capable of being divided.

The screw member 42 is a member being screwed into the female screw portion 323b being provided on the inner peripheral surface of the first opening 321 to close the first opening 321 and hold the driveline 2. The screw member 42 has a screw member inserting path 42b through which the driveline 2 is inserted, a male screw portion 42c provided on the outer peripheral surface, a tip portion 42d to be inserted into the communicating portion 32, a tip contacting portion 42a provided on the inner side of the tip portion 42d to contact the screw member-side contacting portion 41b, and a screw member fitting portion 42e to fit to the sealing member 43. The screw member is arranged between the inner peripheral surface of the communicating portion 32 and the outer peripheral surface of the sealing member 43 and between the inner peripheral surface of the communicating portion 32 and the outer peripheral surface of the chuck member 41. The screw member 42 has, in the holding structure 4, a role of closing the first opening 321, a role of pressing the chuck member 41 and the sealing member 43, and a role of holding the driveline 2. A material for the screw member is not particularly limited as long as the material is capable of achieving the role of closing the first opening 321, the role of pressing the chuck member 41 and the sealing member 43, and a role of holding an insertion target. In the embodiment, the screw member 42 is formed of a metal having a high corrosion resistance, which metal has the hardness equivalent to that of a material forming the fixing device 3 or the hardness lower than that of the material forming the fixing device 3. The metal having the high corrosion resistance may be titanium or a titanium alloy, for example.

The screw member inserting path 42b is a path provided inside the screw member 42 to insert the driveline 2 through the screw member 42. The screw member inserting path 42b is provided from an end of the screw member 42 on the outer side of the living body to the intermediate portion of the screw member 42. The diameter of the screw member inserting path 42b is substantially same as the outer diameter of the driveline 2.

The male screw portion 42c is a portion provided on the outer peripheral surface of the screw member 42 to be screwed into the female screw portion 323b.

The tip portion 42d is a portion to be inserted into the communicating portion 32 of the fixing device 3, and the male screw portion 42c is provided on the outer peripheral surface thereof. In each of the drawings, illustration of threads of the male screw portion 42c may be omitted.

The tip contacting portion 42a is a portion being provided on the inner peripheral surface of the tip portion 42d to contact the screw member-side contacting portion 41b. The tip contacting portion 42a is a portion to contact the screw member-side contacting portion 41b configuring the chuck member 41 and is configured with an inclined surface having an inclined angle being identical to the inclined angle of the inclined surface of the screw member-side contacting portion 41b. The tip contacting portion 42a is formed continuously with the screw member fitting portion 42e. While the tip contacting portion 42a is configured with an inclined surface having an inclined angle being identical to the inclined angle of the inclined surface of the screw-member side contacting portion 41b, the tip contacting portion 42a is not limited thereto. It suffices that the tip contacting portion 42a has a shape capable of transmitting a force from the screw member 42 in a direction in which the chuck member 41 is pushed toward the second opening 322 by contacting at least a part of the tip contacting portion 42a with the screw-member side contacting portion 41b.

Figure 3:
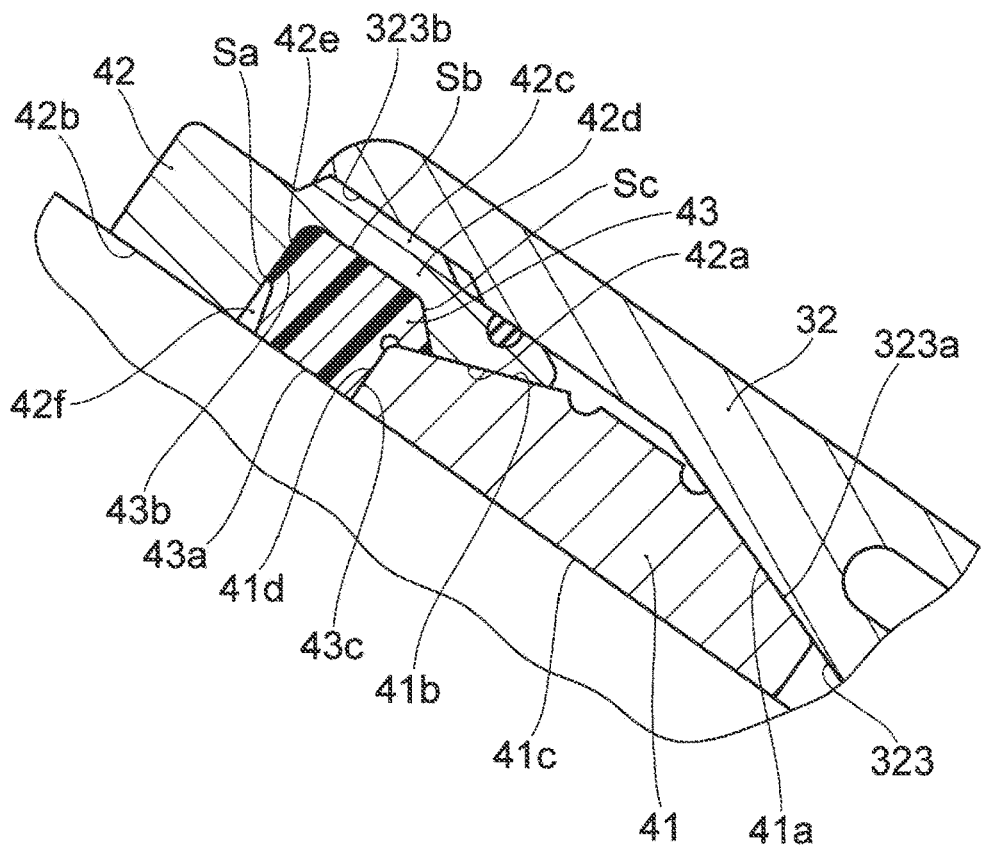
FIG. 3 shows a partially enlarged cross sectional view of the holding structure of the holding mechanism assembly in FIG. 1.

The screw member fitting portion 42e is a portion to fit to the sealing member 43. A pressing surface Sa to press the sealing member 43 in the axial direction of the driveline 2 is provided to the screw member fitting portion 42e. As shown in FIG. 3, the screw member fitting portion 42e has the pressing surface Sa provided at the first opening 321 side and being parallel to the radial direction, a contact surface Sb being parallel to the outer peripheral surface of the sealing member 43, and a contact surface Sc being provided such that the inner diameter of the contact surface Sc is reduced toward the second opening 322 side from the first opening 321 side. The configuration of the screw member fitting portion is not limited to the configuration shown in the embodiment as long as the screw member fitting portion fits to the sealing member and has the pressing surface.

Moreover, the screw member 42 has a receiving portion 42f to receive a deformed portion of the sealing member 43 when the sealing member 43 is pressed and deformed. The receiving portion 42f is provided on the first opening 321 side of the screw member fitting portion 42e and at the inner side (the screw member inserting path 42b side) in the radial direction.

Furthermore, a concave portion 42g to arrange an O-ring 5 is provided on the outer periphery of the screw member 42. The concave portion 42g is provided on the outer peripheral surface of the tip portion 42d. The O-ring 5 is a member provided between the outer peripheral surface of the screw member 42 and the inner peripheral surface of the communicating portion 32 and has a role of assisting the liquidtightness between the screw member 42 and the communicating portion 32. The O-ring 5 may be attached to the inner peripheral surface of the communicating portion 32, not on the outer periphery of the screw member 42.

The sealing member 43 has an inserting member-side pressing portion 43a to elastically press the outer periphery of the driveline 2, a sealing member fitting portion 43b to fit to the screw member 42, and a chuck member-side contact surface 43c to contact the chuck member 41 in the circumferential direction of the driveline 2. The sealing member 43 is a member arranged between the inner peripheral surface of the screw member 42 and the outer peripheral surface of the driveline 2. The sealing member 43 has, in the holding structure 4, a role of holding the driveline 2 by tightening the driveline 2 and a role of achieving the liquidtightness. It suffices that a material for the sealing member is a material capable of having the role of holding the insertion target through the sealing member by tightening the insertion target and the role of achieving the liquidtightness and, as a representative thereof, an elastic material may be used. For example, the material for the sealing member 43 is preferably an elastic resin material, which elastic resin material includes a single synthetic resin composition such as an elastic silicone resin, and a mixture of a synthetic resin and an inorganic compound.

The inserting member-side pressing portion 43a is a member to keep the liquidtightness by contacting and elastically pressing the outer peripheral surface of the driveline 2. In the embodiment, the inserting member-side pressing portion 43a is configured with a surface being parallel to the outer peripheral surface of the driveline 2.

The sealing member fitting portion 43b is a portion to contact the inner surface of the screw member 42. The sealing member fitting portion 43b is a portion to contact the screw member fitting portion 42e of the screw member 42. The sealing member fitting portion 43b has a contact surface being parallel to the pressing surface Sa formed on the first opening 321 side, a contact surface being parallel to the contact surface Sb of the screw member fitting portion 42e, and a contact surface provided such that the inner diameter thereof is reduced toward the second opening 322 side from the first opening 321 side.

The chuck member-side contact surface 43c is a portion to contact the chuck member 41. The chuck member-side contact surface 43c is a portion to contact the sealing member-side contacting portion 41d, and is configured with an inclined surface opposing a part of an inclined surface formed on the first opening 321 side of the chuck member 41 and a surface extended parallel to the radial direction of the communicating portion 32. The chuck member-side contact surface 43c is formed continuously with the sealing member fitting portion 43b. While the chuck member-side contact surface 43c is configured with the inclined surface opposing the part of the inclined surface formed on the first opening 321 side of the chuck member 41 and the surface extended parallel to the radial direction of the communicating portion 32, the chuck member-side contact surface 43c is not limited thereto. It suffices that the chuck member-side contact surface 43c has a shape capable of transmitting a force from the sealing member 43 in a direction in which the chuck member 41 is pushed toward the second opening 322 by contacting at least a part of the chuck member-side contact surface 43c with the chuck member 41.

<Assembling of Holding Structure of Driveline>

Next, an assembling method of the holding mechanism assembly 1 will be explained using FIGS. 1 to 3.

The driveline 2 is inserted through the communicating portion 32 of the fixing device 3. For example, the driveline 2 extending to the outside of the living body from a hole provided in the skin S is inserted through the communicating portion 32 of the fixing device 3 by inserting the driveline 2 from the second opening portion 322 of the fixing device 3 to the first opening 321 side.

Moreover, the chuck member 41 is arranged on the outer periphery of the driveline 2. Specifically, the fitting portion 41c of the second chuck member 412 is contacted with the outer periphery of the driveline 2 while contacting the fitting portion 41c of the first chuck member 411 configuring the chuck member 41 is contacted with the outer periphery of the driveline 2. Joining the joining surface 411a of the first chuck member 411 and the joining surface 412a of the second chuck member 412 causes the chuck member 41 to be arranged on the outer periphery of the driveline 2.

The chuck member 41 is inserted into the communicating portion 32 from the first opening 321 side. While the fixing device-side contacting portion 41a of the chuck member 41 inserted into the communicating portion 32 will contact the communicating portion inclined surface 323a of the communicating portion 32, it does not necessarily have to contact the communicating portion inclined surface 323a of the communicating portion 32 at this time. Next, the sealing member 43 is fitted to the outer periphery of the driveline 2 such that the sealing member 43 is on the upper side (the first opening 321 side) of the chuck member 41. Thereafter, the screw member 42 to which the O-ring 5 is fitted is fitted to the outer periphery of the driveline 2 such that the screw member 42 is on the upper side (the first opening 321 side) of the sealing member 43. Then, the male screw portion 42c of the screw member 42 is screwed into the female screw portion 323b of the communicating portion 32. The screw member 42 moves toward the second opening 322 side of the fixing device 3 by screwing the male screw portion 42c into the female screw portion 323b.

By screwing the male screw portion 42c of the screw member 42 into the female screw portion 323b of the communicating portion 32, the tip contacting portion 42a of the screw member 42 moves toward the second opening 322, and the tip contacting portion 42a presses the screw member-side contacting portion 41b of the chuck member 41. The chuck member-side contact surface 43c of the sealing member 43 presses the sealing member-side contacting portion 41d of the chuck member 41. At that time, in a case that the chuck member 41 has not been contacted with the communicating portion inclined surface 323a of the communicating portion 32, the chuck member 41 moves toward the second opening 322 side and the fixing device-side contacting portion 41a of the chuck member 41 contacts the communicating portion inclined surface 323a of the communicating portion 32. Then, as screwing of the male screw portion 42c into the female screw portion 323b proceeds, the movement of the chuck member 41 is regulated so that a force to bring the driveline 2 into close contact with the fixing device 3 to hold the fixing device 3 is generated. This makes it possible to assemble the holding mechanism assembly 1 comprising the holding structure 4 having a high close contactability.

The above-described assembling procedure is one example, so that the assembling procedure up to causing the male screw portion 42c of the screw member 42 to be screwed into the female screw portion 323b of the communicating portion 32 is not particularly limited.

The structure of the above-described holding mechanism assembly 1 is merely one example, so that the structure of the holding mechanism assembly is not limited to the embodiment.

Next, the fixing device 3 in the embodiment will be explained in more detail.

The fixing device 3 is fixed beneath the skin of the living body. As described above, the fixing device 3 in the embodiment, as shown in FIG. 1, is fixed to the skin S beneath the skin of the living body by a part of the skin S being anchored (fixed) onto the surface of the fixing device 3. While the fixing device 3 in the embodiment, as described above, is used to arrange the driveline 2 in the living body, the usage of the fixing device 3 is not particularly limited thereto as long as the fixing device 3 is fixed beneath the skin of the living body. In the embodiment, the fixing device 3 may also function as an access port fixed to the skin S by an inserting member such as the driveline 2 (also called below the inserting member 2) to connect outside and inside of the living body so as to access from outside of the living body to inside of the living body. The fixing device 3 is arranged under the incised skin S in the surroundings of a hole formed in the living body to insert the inserting member therethrough. The fixing device 3 induces the skin tissues of the incised skin S to the fixing device 3 and is fixed beneath the skin of the living body.

In the embodiment, as shown in FIGS. 1 and 2, the fixing device 3 has the fixing portion 31 to be fixed to the skin S and the communicating portion 32 through which the inserting member 2 is inserted to communicate the inside and the outside of the living body. While the communicating portion 32 may be configured to have the above-described structure as one example, the communicating portion 32 is not limited to the above-described structure.

Figure 4:
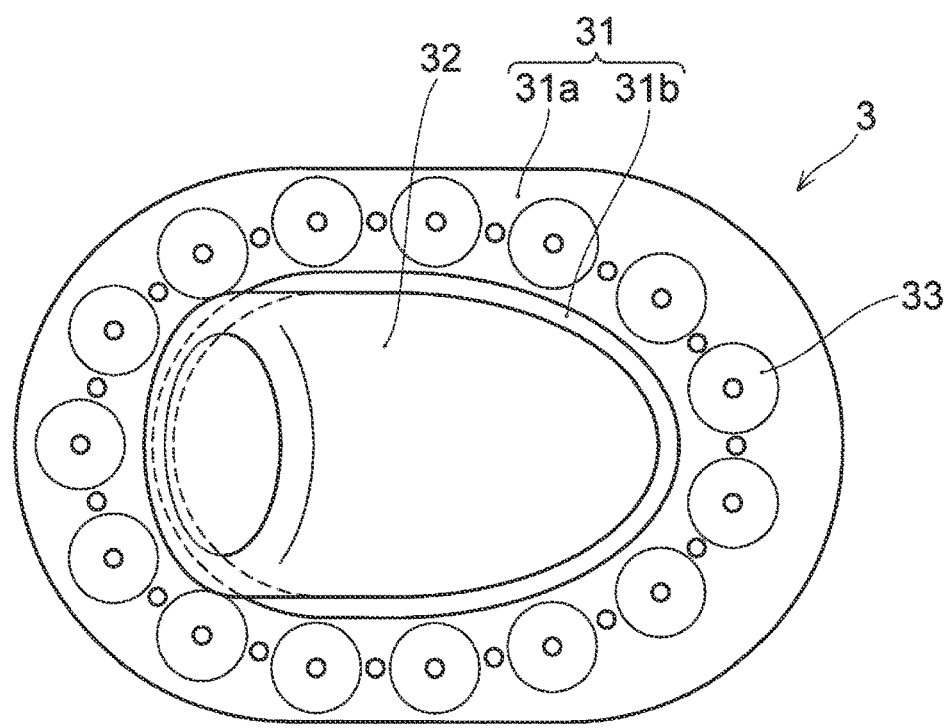
FIG. 4 shows a top view of the fixing device according to one embodiment of the invention.

The fixing portion 31 of the fixing device 3 is fixed to the skin S by inducing the skin tissues of the incised skin S to the fixing portion 31. In the embodiment, as shown in FIGS. 1, 2, and 4, the fixing portion 31 is extended from the communicating portion 32 outwardly in the radial direction of the communicating portion 32 at the end on the living body-side of the communicating portion 32. In the embodiment, the fixing portion 31 is formed in a flange shape to surround the communicating portion 32. The fixing portion 31 is formed in a plate shape provided with the communication path 323 of the communicating portion 32 passing therethrough. As shown in FIGS. 1 and 2, in the fixing portion 31, a plurality of countersink portions 33 each being a concave portion are provided on a first surface on the first opening 321 side. In the countersink portion 33, the skin tissues can enter the space of the concave portion, which countersink portion 33 is provided in a grinding bowl shape.

Figure 5:
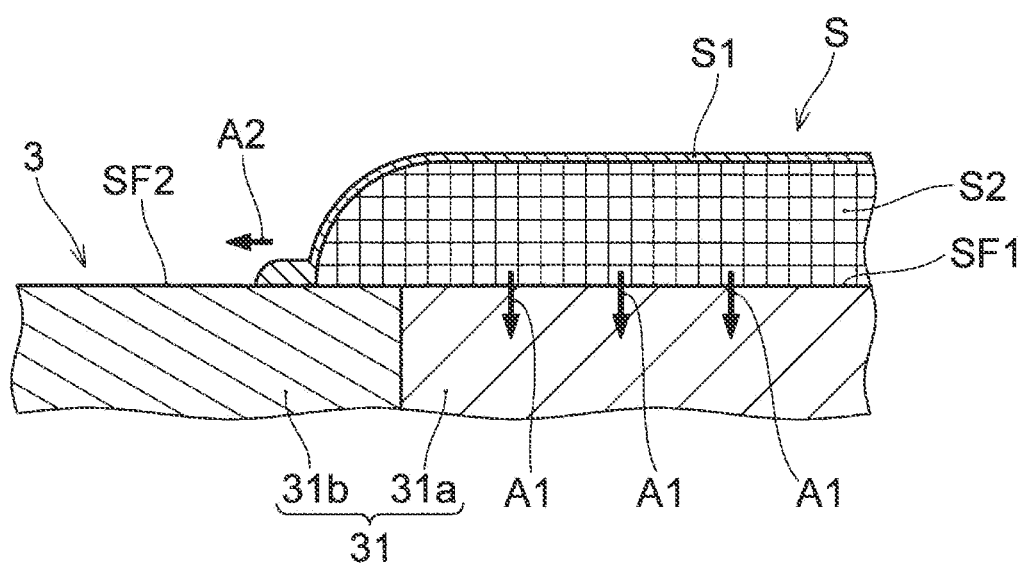
FIG. 5 shows a schematic view of the skin being fixed to the fixing device in FIG. 4.

The fixing portion 31 of the fixing device 3, as shown in FIGS. 4 and 5, has a porous portion 31a capable of inducing cells to the space of the porous portion 31a and a flat portion 31b that allows the cells to be adhered thereto.

The porous portion 31a has a plurality of pores having a pore diameter to induce the cells into the pores. The porous portion 31a is, of the fixing portion 31, a part in which a large number of pores into which the cells can enter to be fixed thereto are formed. While a single pore that allows the cells to invade thereinto can be provided in a plurality in the porous portion 31a, the porous portion 31a preferably has a porous layer in which a plurality of pores are communicatively connected three-dimensionally. The skin S is fixed to the porous portion 31a by inducing the cells in the thickness direction of the porous portion 31a (in the downward direction in FIG. 5) to pores (air gaps) formed in the porous portion 31a. As long as the cells can invade and grow in the porous portion 31a, the material for the porous portion 31a or the size of the pores is not particularly limited. For the porous portion 31a, a porous material known in the medical field, such as a mesh-shaped titanium fiber may be used, for example. As the porous portion 31a is a part fixing the fixing device 3 to the skin, the porous portion 31a is preferably a hard member and is more preferably made of a metal such as titanium. Moreover, it is preferable that the porous portion 31a is provided integrally with the fixing portion 31 and it is more preferable that the porous portion 31a is provided integrally with the fixing device 3.

The flat portion 31b has a substantially flat surface and has primarily a function of causing the cells to adhere to the surface of the flat portion 31b. "Adhesion" of the cells means that, in the flat portion 31b, the cells do not invade deeply into the flat portion 31b in the thickness direction of the fixing portion 31 as in the porous portion 31a, but the cells grow along the surface of the flat portion 31b (in the left direction in FIG. 5) to adhere to the surface SF2 (see FIG. 5) of the flat portion 31b. The flat portion 31b does not have pores into which the cells invade to be fixed thereto and the flat portion 31b does not have a porous surface. With respect to the adhesion between the flat portion 31b and the cell tissues, in a case of separating the adhered tissues from the flat portion 31b with applying load, they adhere such that they can be separated from the interface between the flat portion 31b and the cell tissues without the cell tissues being destructed.

Moreover, the flat portion 31b is substantially flat, so that the skin tissues are not inhibited from growing along the surface SF2 of the flat portion 31b. Unlike the porous portion 31a being porous, the surface SF2 of the flat portion 31b may be a substantially flat and smooth surface, or may have a fine uneven pattern formed by surface treatment. The uneven height of the uneven pattern in a case of the uneven pattern being formed on the surface SF2 of the flat portion 31b is not particularly limited as long as the growth of the cells along the surface SF2 of the flat portion 31b is not inhibited. In the flat portion 31b, the distance from the middle position between the bottom of the concave portion of the uneven pattern and the vertex of the convex portion of the uneven pattern to the bottom of the concave portion or to the vertex of the convex portion is preferably set to be less than or equal to 100 µm, for example. A material for the flat portion 31b is not particularly limited as long as the cells can adhere to the surface SF2 of the flat portion 31b. The flat portion 31b may be configured by a material having a high biocompatibility, such as titanium or a titanium alloy, for example. Furthermore, the flat portion 31b may be made to have a desired surface condition by providing the material having the high biocompatibility with a publicly-known surface treatment such as a mirror surface process or a blasting process (particularly a grit blasting process). The flat portion 31b, unlike the porous portion 31a, for example, may be made to have a solid portion along the surface SF2 of the flat portion 31b, or the entire flat portion 31b may be made to be solid. The flat portion 31b has a predetermined area in which the adhesion between the skin tissues and the flat portion 31b may be secured. In the embodiment, the flat portion 31b extends for between 0.2 mm and 0.3 mm as a width toward the opposite side to the porous portion 31a from the boundary between the porous portion 31a and the flat portion 31b. However, the above-mentioned width may be greater than or equal to 0.1 mm, and when the width is greater than or equal to 1 mm, adherability increases. The width of the flat portion 31b may be set appropriately in accordance with the usage or the applied part of the fixing device 3.

As shown in FIGS. 4 and 5, the porous portion 31a and the flat portion 31b are provided adjacent to each other, and a virtual surface SF1 (see FIG. 5) of the porous portion 31a and a surface SF2 of the flat portion 31b are substantially flush with each other. The porous portion 31a is porous, so that, strictly speaking, the surface of the porous portion 31a has a depth in the depth direction of the pores and has, not a flat, but a three-dimensional structure as viewed microscopically. The virtual surface SF1 of the porous portion 31a is a virtual surface connecting the outermost portion of the surface of the porous portion 31a (the upper end in FIG. 5) in a horizontal direction and is a schematic surface as the outer side when the porous portion 31a is grasped macroscopically. In a case that the flat portion 31b has an uneven pattern, the surface SF2 of the flat portion 31b is a virtual surface connecting the vertices of the uneven pattern. Moreover, "substantially flush" means that, in the boundary between the adjacently-arranged porous portion 31a and flat portion 31b, no clear step is formed, and a surface is formed such that the cells are not inhibited from growing toward the flat portion 31b from the porous portion 31a. No step inhibiting the cells from growing along the surfaces SF1 and SF2 is provided at the boundary between the porous portion 31a and the flat portion 31b.

As shown in FIG. 5, in the fixing portion 31, the porous portion 31a and the flat portion 31b are arranged adjacent to each other such that they are substantially flush with each other. In this way, the skin tissues are induced in the thickness direction of the porous portion 31a (the direction being perpendicular to the virtual surface SF2 of the porous portion 31a) by the porous portion 31a, and thereby, enhances adhesion of the fixing device 3 with the skin S. Moreover, the growth of the skin S along the surface SF2 of the fixed portion 31 can be promoted by the flat portion 31b. Unlike the porous portion 31a, the flat portion 31b does not have pores in which bacteria propagates or to which foreign substances fix, so that an occurrence of inflammation in the cell tissues due to substances causing an occurrence of inflammation in the cells, such as bacteria or foreign substances, is suppressed. Improvement in fixability to the skin S of the fixing device 3 by the porous portion 31a and promotion of the growth of the tip of the skin S along the surface SF2 of the flat portion 31b, such as an epidermis layer S1 of the skin S, can be both satisfied. For example, in the porous portion 31a, as shown with an arrow A1 in FIG. 5, the tissues of a dermis layer S2 invade thereinto in the thickness direction of the porous portion 31a, enhancing the anchoring effect. In the flat portion 31b, the cell tissues adhere to the surface thereof, so that it can be suppressed that the substances causing an occurrence of inflammation in the cells, such as bacteria or foreign substances, reaches to the porous portion 31a. Moreover, the cuticle-shaped tip (keratin) of the epidermis layer S1 of the skin S being positioned in the flat portion 31b causes the growth of the skin tissues to be promoted along the surface SF2 as shown with an arrow A2 in FIG. 5, rather than in the thickness direction of the flat portion 31b. Furthermore, immediately after the fixing device 3 is fixed beneath the skin by a surgical operation, most or the entirety of the porous portion 31a is covered with the skin S. The flat portion 31b being exposed to the external environment is not porous (may be formed with a solid material, for example), and the skin S is adhered to the surface SF2 of the flat portion 31b. Consequently, it is considered that bacteria from the exterior is difficult to reach the dermis layer S2. Therefore, it is considered that, in a case of the fixing device 3 in the embodiment, an inflammatory response of the skin due to bacteria invading from the external environment is unlikely to occur, this makes it possible to maintain a good skin condition after the fixing device 3 is fixed beneath the skin.

In the embodiment, as shown in FIG. 4, the porous portion 31a is provided on the outer side of the flat portion 31b with a predetermined reference position as the center, and the porous portion 31a and the flat portion 31b are continuously provided in the peripheral direction, respectively. In other words, as shown in FIG. 4, annular flat portion 31b is provided around the predetermined reference position as the center continuously in the peripheral direction, and annular porous portion 31a is provided on the outer side of the flat portion 31b continuously in the peripheral direction. The flat portion 31b is preferably provided on the outer side of the porous portion 31a with respect to the direction in which the skin grows. The porous portion 31a is provided continuously with respect to the flat portion 31b in a direction being away from the reference position. The predetermined reference position may be set to be a position corresponding to the position of the hole of the living body through which the inserting member 2 is inserted when the fixing device 3 is fixed beneath the skin, such as the central portion of the fixing device 3, for example. In the embodiment, the communicating portion 32 to communicate the inside of the living body and the outside of the living body is provided on the inner side of the flat portion 31b, and the predetermined reference position is set to be the position at which the communicating portion 32 is provided.

In the embodiment, the porous portion 31a is provided on the outer side of the flat portion 31b with the predetermined reference position as the center. In this case, when the fixing device 3 is fixed beneath the skin, at the position of the porous portion 31a provided on the outer side of the fixing portion 31 of the fixing device 3, the skin tissues invade into and induced to the porous portion 31a in the thickness direction of the porous portion 31a, so that the fixing device 3 is fixed beneath the skin. The porous portion 31a is provided in a range being required to obtain a fixing power needed to fix the fixing device 3 to the living body. Moreover, in the embodiment, as shown in FIG. 4, the porous portion 31a is provided on the outer side of the flat portion 31b continuously in the peripheral direction. In this case, in a predetermined belt-shaped region having a predetermined width from the outer periphery of the fixing device 3, the porous portion 31a and the skin S adhere tightly to with each other to stabilize the fixing device 3 beneath the skin. Moreover, in the flat portion 31b being positioned on the inner side of the porous portion 31a, the tip of the skin S grows toward the predetermined reference position (toward the communicating portion 32 in the embodiment) while adhering to the flat portion 31b. Consequently, after the fixing device 3 is fixed beneath the skin, the skin S easily grows toward the central portion of the fixing device 3, such as the communicating portion 32, and making it possible to cover the fixing portion 31 of the fixing device 3 by the skin S early, so that the treatment of the wound is promoted.

DESCRIPTION OF REFERENCE NUMERALS

1 HOLDING MECHANISM ASSEMBLY
2 DRIVELINE (INSERTING MEMBER)
21 COOLING WATER CIRCULATION PATH
22 POWER CABLE
3 FIXING DEVICE
31 FIXING PORTION
31a POROUS PORTION
31b FLAT PORTION
32 COMMUNICATING PORTION
321 FIRST OPENING
322 SECOND OPENING
323 COMMUNICATION PATH
323a COMMUNICATING PORTION INCLINED SURFACE
323b FEMALE SCREW PORTION
33 COUNTERSINK PORTION
4 HOLDING STRUCTURE
41 CHUCK MEMBER
41a FIXING DEVICE-SIDE CONTACTING PORTION
41b SCREW MEMBER-SIDE CONTACTING PORTION
41c FITTING PORTION
41d SEALING MEMBER-SIDE CONTACTING PORTION
41e CONCAVE PORTION
411 FIRST CHUCK MEMBER
411a JOINING SURFACE
412 SECOND CHUCK MEMBER
412a JOINING SURFACE
42 SCREW MEMBER
42a TIP CONTACTING PORTION
42b SCREW MEMBER INSERTING PATH
42c MALE SCREW PORTION
42d TIP PORTION
42e SCREW MEMBER FITTING PORTION
42f RECEIVING PORTION
42g CONCAVE PORTION
43 SEALING MEMBER
43a INSERTING MEMBER-SIDE PRESSING PORTION
43b SEALING MEMBER FITTING PORTION
43c CHUCK MEMBER-SIDE CONTACT SURFACE
5 O-RING
S SKIN
S1 EPIDERMIS LAYER
S2 DERMIS LAYER
Sa PRESSING SURFACE
Sb CONTACT SURFACE
Sc CONTACT SURFACE
SF1 VIRTUAL SURFACE OF POROUS PORTION
SF2 SURFACE OF FLAT PORTION

The invention claimed is:

1. A fixing device to be fixed beneath skin of a living body, the fixing device comprising: a porous portion capable of inducing cells to the porous portion and a flat portion that allows the cells to adhere to the flat portion, the porous portion and the flat portion provided adjacent to each other, wherein the porous portion is provided on an outer side of the flat portion with a predetermined reference position as a center, and the porous portion and the flat portion are continuously provided in the peripheral direction, respectively,
wherein a virtual surface of the porous portion and a surface of the flat portion are substantially flush with each other, wherein the flat portion is configured to be entirely solid, wherein the flat portion is configured that the skin is adhered to the flat portion along the surface of the flat portion, and wherein the flat portion is configured by a substantially flat and smooth surface such that the skin adhered to the flat portion along the surface of the flat portion is separable from an interface between the flat portion and cell tissues of the skin.

2. The fixing device according to claim 1, wherein a communicating portion to communicate inside of the living body and outside of the living body is provided on an inner side of the flat portion.

3. The fixing device according to claim 1, wherein the porous portion and the flat portion are made of a metal.

4. A fixing device to be fixed beneath skin of a living body, the fixing device comprising: a porous portion capable of inducing cells to the porous portion and a flat portion that allows the cells to adhere to the flat portion, the porous portion and the flat portion provided adjacent to each other, wherein the porous portion is provided on an outer side of the flat portion with a predetermined reference position as a center, and the porous portion and the flat portion are continuously provided in the peripheral direction, respectively, wherein a virtual surface of the porous portion and a surface of the flat portion are substantially flush with each other, wherein the flat portion is configured to be entirely solid, wherein the flat portion is configured that the skin is adhered to the flat portion along the surface of the flat portion, and wherein the flat portion is configured by a fine uneven pattern in which a distance from a middle position between a bottom of a concave portion of the uneven pattern and a vertex of a convex portion of the uneven pattern to the bottom of the concave portion or to the vertex of the convex portion is less than or equal to 100 μm, such that the skin adhered to the flat portion along the surface of the flat portion is separable from an interface between the flat portion and cell tissues of the skin.

5. The fixing device according to claim 4, wherein a communicating portion to communicate inside of the living body and outside of the living body is provided on an inner side of the flat portion.

6. The fixing device according to claim 4, wherein the porous portion and the flat portion are made of a metal.

* * * * *